US006502532B2

(12) United States Patent
Sjölin

(10) Patent No.: US 6,502,532 B2
(45) Date of Patent: Jan. 7, 2003

(54) ANIMAL BANDAGE DEVICE

(76) Inventor: Nils Erik Sjölin, Torneagatan 62, S-164 79 Kista (SE)

( * ) Notice: Subject to any disclaimer, the term of this patent is extended or adjusted under 35 U.S.C. 154(b) by 0 days.

(21) Appl. No.: 10/095,194

(22) Filed: Mar. 8, 2002

(65) Prior Publication Data

US 2002/0124812 A1 Sep. 12, 2002

Related U.S. Application Data

(60) Provisional application No. 60/274,767, filed on Mar. 9, 2001.

(51) Int. Cl.[7] .......................... A01K 13/00; A61F 11/00

(52) U.S. Cl. ........................ 119/850; 119/174; 119/814; 128/866

(58) Field of Search ................................ 119/174, 650, 119/651, 653, 712, 856, 850, 814, 837; 602/53, 74, 76; 128/864, 866; D30/144; 54/80.1

(56) References Cited

U.S. PATENT DOCUMENTS 2,136,115 A * 11/1938 McCaleb .................... 119/850
3,823,713 A * 7/1974 Shah ............................. 2/174
4,233,942 A * 11/1980 Williams .................... 119/814
4,964,264 A * 10/1990 Adams ....................... 119/850
5,163,272 A * 11/1992 Finley et al. ................ 54/80.1
5,809,573 A * 9/1998 Bary .......................... 128/866
D417,315 S * 11/1999 Lowry ....................... D30/144
6,195,806 B1 * 3/2001 Campbell ................... 128/866
6,314,961 B1 * 11/2001 Barnes ....................... 128/864

FOREIGN PATENT DOCUMENTS

FR 2589676 A1 * 5/1987 ............ A61D/9/00

* cited by examiner

*Primary Examiner*—Charles T. Jordan
*Assistant Examiner*—Kimberly S. Smith
(74) *Attorney, Agent, or Firm*—Fasth Law Offices; Rolf Fasth

(57) ABSTRACT

The method is for treating ear injuries of an animal with a bandage device that is mounted to the animal's head. The bandage device has a first holder portion and a first disc attached thereto. The first holder portion has a first opening and a second opening defined therein. The first ear is inserted through the first opening and the ear is placed on the first disc disposed over the second opening. A first layer is attached on the first holder portion so that a net of the first layer is aligned with the first disc. The net is placed on an inside of the first ear so that the ear is captured between the net and the first disc.

6 Claims, 4 Drawing Sheets

ANIMAL BANDAGE DEVICE

PRIOR APPLICATION

This application claims priority from U.S. Provisional Patent Application Serial No. 60/274,767; filed Mar. 9, 2001.

TECHNICAL FIELD

The present invention relates to a method and device for treating an animal ear injury.

BACKGROUND AND SUMMARY OF THE INVENTION

Dogs sometimes have irritation in the ears that may result in substantial swelling due to blood and other substances accumulating inside the skin of the ears. Conventional methods of treating such irritation require cumbersome and agonizing stitching procedures. The healing process is sometimes very long due to infections that may result from the dog's normal movements and scratching. There is a need for a method and device that provide an improved treatment method.

The present invention is a reliable method for eliminating the need for stitching procedure and shortening the healing process. More particularly, the method of the present invention is for treating ear injuries of an animal with a bandage device that is mounted to the animal's head. The bandage device has a first holder portion and a first disc attached thereto. The first holder portion has a first opening and a second opening defined therein. The first ear is inserted through the first opening and the ear is placed on the first disc disposed over the second opening. A first layer is attached on the first holder portion so that a net of the first layer is aligned with the first disc. The net is placed on an inside of the first ear so that the ear is captured between the net and the first disc.

DETAILED DESCRIPTION

Figure 1:
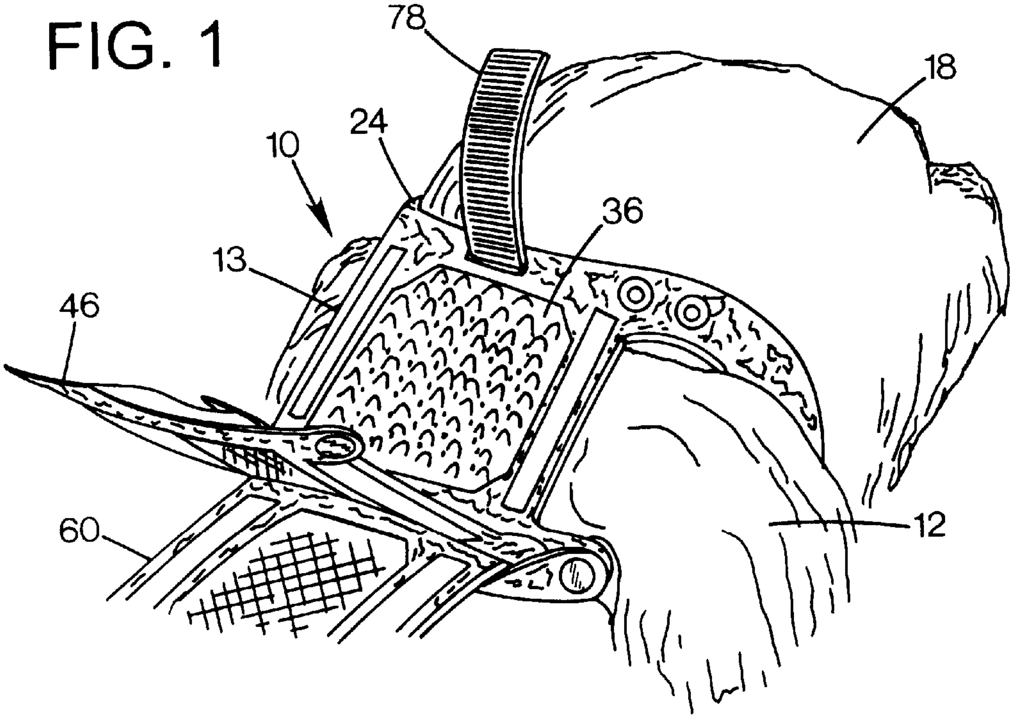
FIG. 1 is a perspective rear view of the bandage device of the present invention mounted on a dog's head.

With reference to FIGS. 1–7, the animal bandage device 10 of the present invention is particularly suited for treating injuries, such as aural hematoma, to a dog's ear 12.

The device 10 has a band 14 that may be attached to a lock 16 after the device 10 has been mounted around the dog's head 18 so that the ears 12, 13 protrude through openings 20, 22 defined by an oval-shaped holder section 24.

Figure 5:
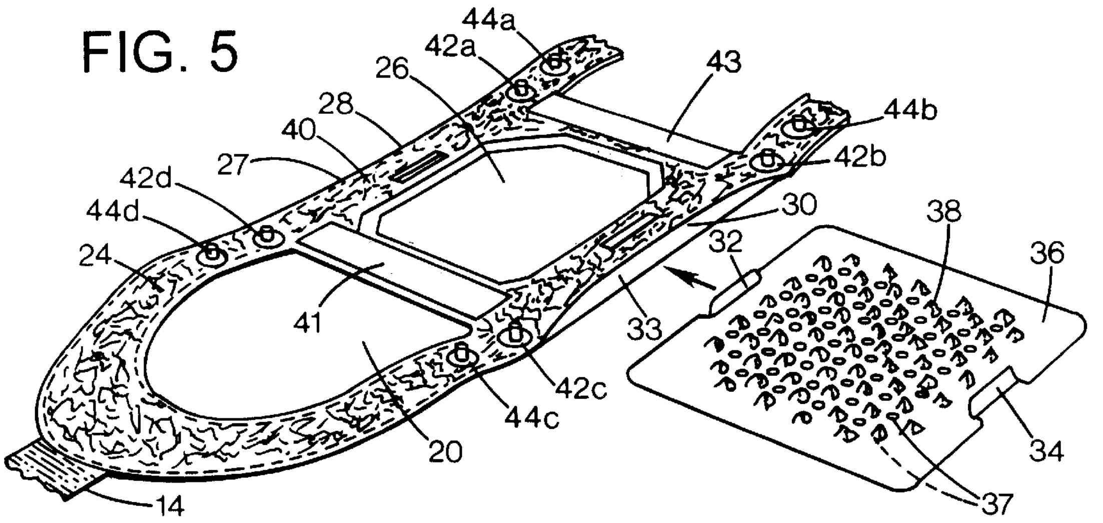
FIG. 5 is a detailed perspective view of a portion of the bandage device.

As best seen in FIG. 5, the holder section 24 also has an opening 26 defined therein between the openings 20, 22. On each side of the opening 26, at a mid section 27 of the section 24, the section 24 has opposite slits 28, 30 defined therein to receive upwardly protruding tabs 32, 34 of a plastic disc 36. One function of the tabs 32, 34 is to act as spacers to make sure there is a gap formed when a net segment 54 is applied to the disc 36, as described in detail below. The tabs 32, 34 may be inwardly sloping so that the size of the gap may be adjusted by exerting a slight pressure on the tabs 32, 34, if desired. The disc 36 is filled with surface protrusions 38 and may be inserted through a slip opening 33 and attached to the mid section 27 by engaging the tabs 32, 34 with the slits 28, 30, respectively, so that the protrusions 38 are disposed in the opening 26. An upper side 40 of the holder section 24 has male fasteners 42*a*–*d* and 44*a*–*d*. The side 40 may also have tape adhesive fasteners 41, 43.

Figure 6:
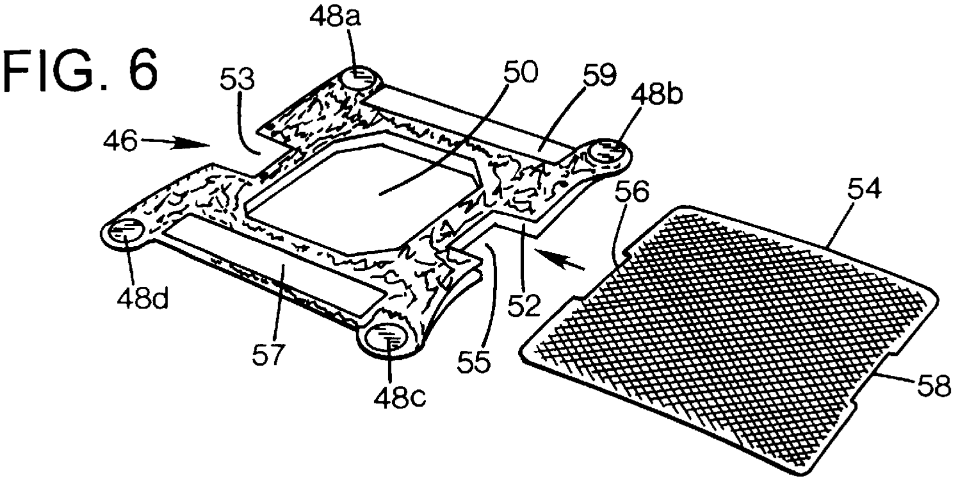
FIG. 6 is a detailed perspective view of a portion of the bandage device.

As best shown in FIG. 6, a mid-layer 46 has female fasteners 48*a*–*d* that correspond to the male fasteners 42*a*–*d* so that the mid-layer 46 may be snapped onto the mid-section 27. The mid-layer 46 may include a double-side tape on the upper side and the under side of the layer 46. The layer 46 has an opening 50 and a slit opening 52 defined therein for receiving the net segment 54 so that the net segment 54 is disposed inside the opening 50 when the segment 54 is fully inserted into the slit opening 52 but on top of the disc 36 so that a gap is formed therebetween. As outlined below, the gap ensures that the protrusions 38 does not exert too high of a pressure on the dog's ear. The layer 46 may have adhesive tape fasteners 57, 59 and side cavities, 53, 55 defined at each side of the layer 46.

Figure 7:
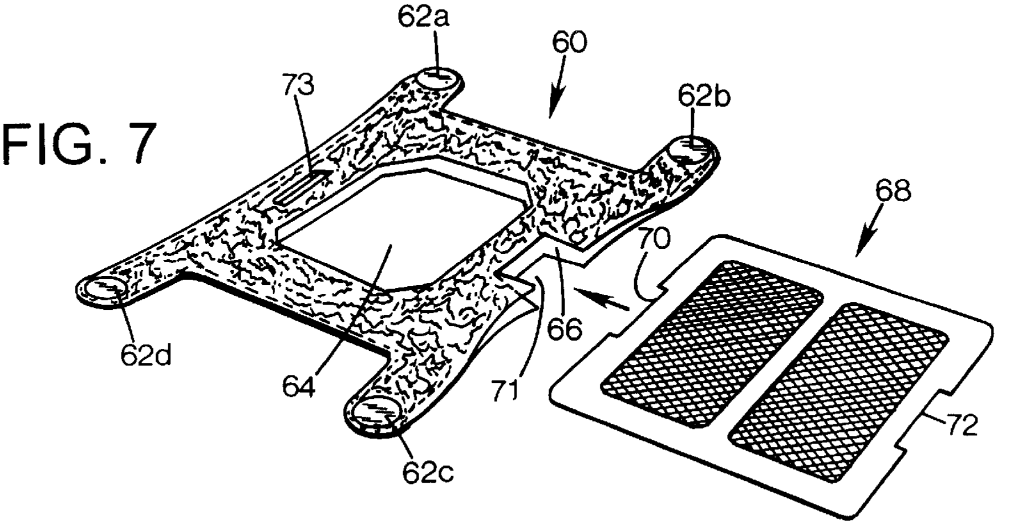
FIG. 7 is a detailed perspective view of a portion of the bandage device.

As best shown in FIG. 7, a top layer 60 has female fasteners 62*a*–*d* that correspond to the male fasteners 44*a*–*d* so that the layer 60 may be snapped onto the holder section 24 and the mid-layer 46 by engaging the fasteners. The layer 60 has an opening 64 defined therein and a slit opening 66 for receiving a reinforced segmented net member 68. The net member 68 has opposite recesses 70, 72. The layer 60 has a side cavity 71 and an opening 73 defined therein.

Figure 2:
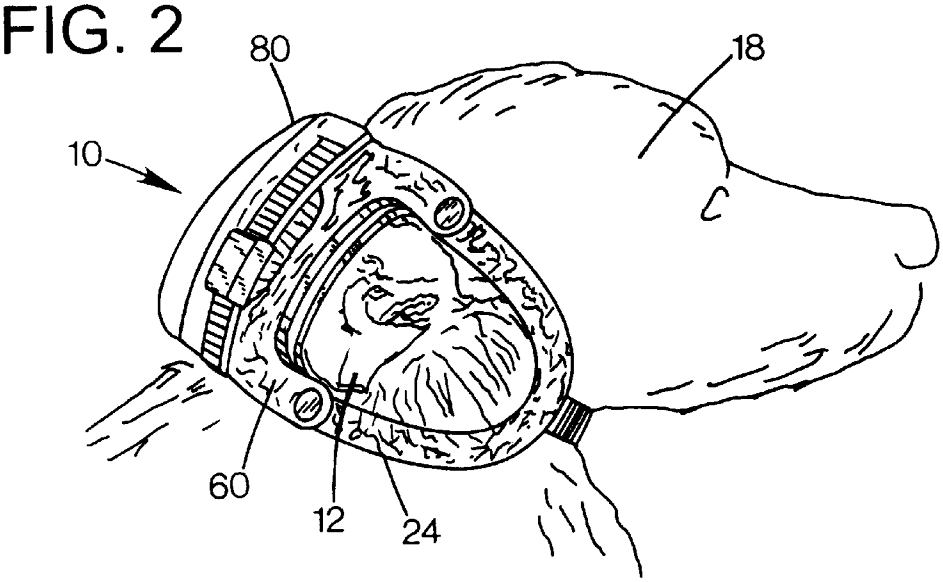
FIG. 2 is a perspective side view of the bandage device shown in FIG. 1.
Figure 3:
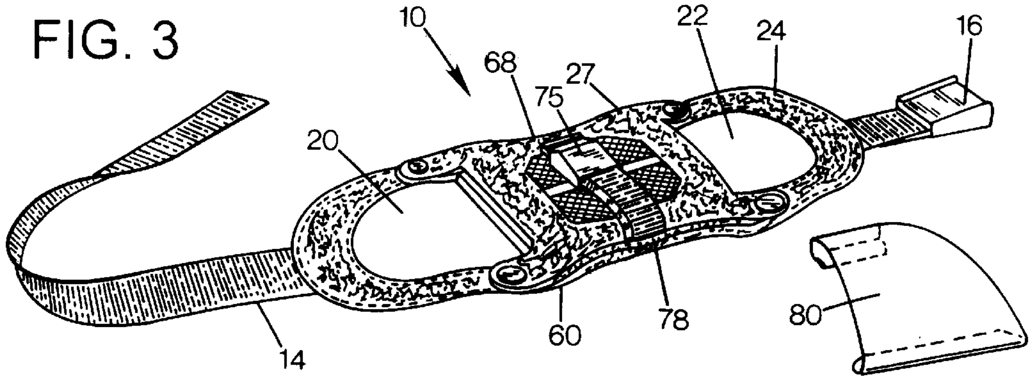
FIG. 3 is a perspective view of the bandage device in a folded position.
Figure 4:
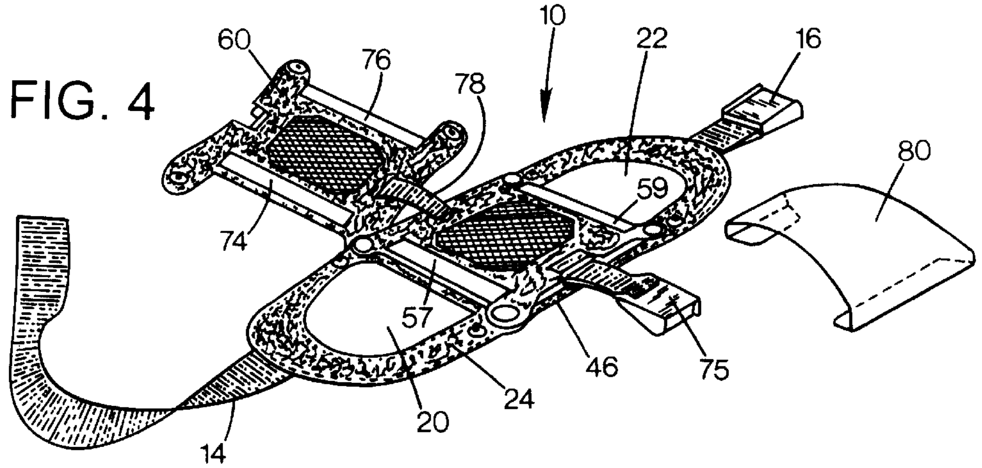
FIG. 4 is a perspective view of the bandage device in a partially unfolded position.

FIG. 4 shows the layer 46 snapped onto the mid-section 27 and an underside of the top layer 60 so that tape fasteners 74, 76 are shown. All the tape fasteners may have a removable cover tape. One function of the tape fasteners is to hold the ear in place in the bandage. If the dog has a tendency to shake its head violently, it may be necessary to also attach a sticky fabric to both sides of the dog's ear to prevent the ear from sliding out of the bandage device 10. A band 78 may be slid through the opening 73 and the side cavities 53, 55, 56, 58, 70, 72 and 71 and fastened to locking device 75 to firmly hold all the various layers to the holder portion 24. A transparent plastic protector 80 may be snapped onto the device 10, as best shown in FIG. 2.

In operation, the bandage device 10 is mounted on the dog's head 18, by fastening the band 14 into the lock fastener 16. One of the ears 12 of the dog should be inserted through the openings 20, 22 and the upper side of the ear 12 is placed on the disc 36 so that the outside or upside of the earflap rests on the disc. The protrusions 38 make sure there is air next to the ear 12 so that there is sufficient air circulation. The disc 36 also has a plurality of orifices 37 between the protrusions to further improve air circulation. The protrusions 38 also provide a pressure on the ear that is equivalent to the pressure provided by conventional sutures. The layer 46 is then attached to the holder portion 24 by the fasteners 42*a*–*d*, 48*a*–*d* so that the net 54 is applied to the inside of the ear. The adhesive tape fasteners also aid in the attachment. It is usually the inside of the ear that has the accumulation of blood that requires treatment. If the other ear 13 also needs treatment, the other ear 13 may be put on top of the net 54 of the layer 46. The top layer 60 is then snapped onto the fasteners 44*a–d* so that the second ear 13 is captured between the top layer 60 and the middle layer 46 while the first ear 12 is captured between the holder portion 24 and the mid layer 46. The band 78 is then locked to the locking device 75 to firmly hold both ears 12, 13 in place during the healing process. Because the net 68 is reinforced, the net 68 will provide an evenly distributed pressure over the entire device 10 and the ears when the band 78 is tightened. The cover 80 may then be snapped in place to reduce the risk of the dog removing the device 10 with its pawns. Because no stitching is used, there is less risk that scars will appear on the ears after the treatment is completed.

Figure 8:
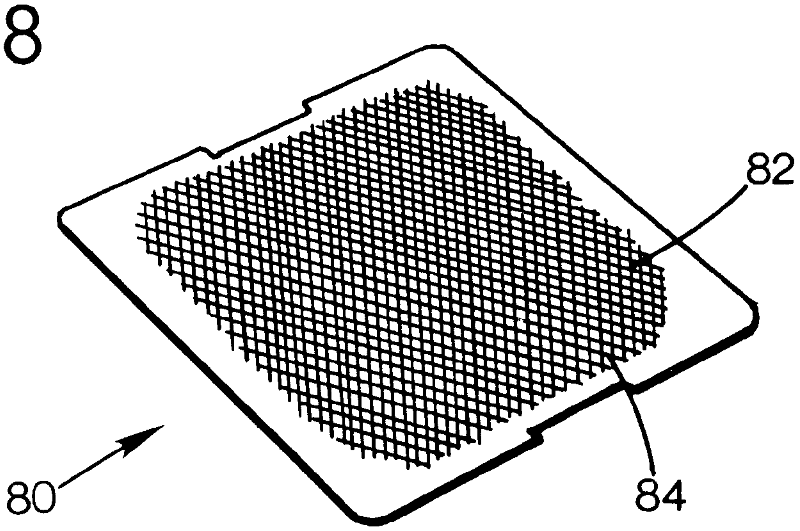
FIG. 8 is a detailed perspective view of an alternative portion of the bandage device.

FIG. 8 shows an alternative disc 80 that is similar to the disc 36 except that the disc 80 is plane and has a net 82 with a plurality of orifices 84 through air may flow.

While the present invention has been described in accordance with preferred compositions and embodiments, it is to be understood that certain substitutions and alterations may be made thereto without departing from the spirit and scope of the following claims.

I claim:

1. A method for treating ear injuries of an animal with a bandage device, comprising:

providing a bandage device mounted on a head of the animal, the bandage device having a first holder portion and a first disc attached to the first holder portion, the first holder portion having a first opening and a second opening defined therein, the first disc having a net with a plurality of orifices defined therein, the first disc being placed over the second opening;

inserting a first ear of the animal through the first opening and bending the first ear over the head;

placing an outside of the first ear on the first disc and over the second opening;

attaching a first layer on the first holder portion so that a net of the first layer is aligned with the first disc;

placing the net of the first layer on an inside of the first ear; and capturing the first ear between the net of the first layer and the first disc.

2. The method according to claim 1 wherein the method further comprises attaching a second layer on the first holder portion and placing a second ear of the animal on the first layer.

3. The method according to claim 2 wherein the method further comprises providing the second layer with a net portion and placing an outside of the second ear on the net portion of the first layer.

4. The method according to claim 1 wherein the method further comprises providing the first disc with tabs to create a gap between the first disc and the net when the net is placed on top of the first disc.

5. The method according to claim 2 wherein the method further comprises inserting a second net device into the second layer.

6. The method according to claim 3 wherein the method further comprises placing a second layer over the second ear.

* * * * *